United States Patent [19]

Erpenbach et al.

[11] 4,444,624
[45] Apr. 24, 1984

[54] PROCESS FOR SEPARATING ACETONE FROM CARBONYLATION MIXTURES

[75] Inventors: Heinz Erpenbach, Cologne; Klaus Gehrmann; Winfried Lork, both of Erftstadt; Peter Prinz, Hürth, all of Fed. Rep. of Germany

[73] Assignee: Hoechst Aktiengesellschaft, Fed. Rep. of Germany

[21] Appl. No.: 412,225

[22] Filed: Aug. 27, 1982

[30] Foreign Application Priority Data

Sep. 11, 1981 [DE] Fed. Rep. of Germany ....... 3136027

[51] Int. Cl.$^3$ .......................... B01D 3/40; C07C 45/83
[52] U.S. Cl. ...................................... 203/61; 203/70; 203/82; 203/84; 568/387; 568/411
[58] Field of Search .................... 203/61, 71, 84, 68, 203/70, 52, 82, 81; 568/411, 387

[56] References Cited

U.S. PATENT DOCUMENTS

| | | | |
|---|---|---|---|
| 2,704,271 | 3/1955 | Harrison et al. | 203/70 |
| 3,591,463 | 7/1971 | Copelin | 203/61 |
| 3,871,970 | 3/1975 | Nienburg et al. | 203/61 |
| 4,252,748 | 2/1981 | Hoch et al. | 568/411 |
| 4,364,869 | 12/1982 | Muller et al. | 203/61 |

FOREIGN PATENT DOCUMENTS 53249 6/1982 European Pat. Off. ............ 203/68

Primary Examiner—Wilbur L. Bascomb, Jr.
Attorney, Agent, or Firm—Connolly and Hutz

[57] ABSTRACT

The disclosure relates to a process for separating acetone from reaction mixtures originating from the reaction of methyl acetate and/or dimethylether with carbon monoxide and optionally hydrogen in the presence of a catalyst system consisting of carbonyl complexes of noble metals of group VIII of the Periodic System of the elements, acetic acid, an organophosphorus or organonitrogen compound, methyl iodide and optionally carbonyl-yielding compounds of common metals. To this end, the disclosure provides for the reaction mixture containing acetic anhydride, acetic acid, ethylidene diacetate, methyl iodide, acetone and methyl acetate which is distilled off from the catalyst solution, or just its low boiler fraction consisting of methyl acetate, methyl iodide and acetone to be subjected wholly or partially to an extractive distillation with acetic acid and for pure methyl iodide to be distilled off; for an acetone/methyl acetate mixture to be distilled off from the acetic acid extract; for this mixture to be separated in known fashion and for the acetic acid extractant to be recycled into the extraction stage, if desired after separation of the final reaction products comprised of acetic anhydride; ethylidene diacetate and acetic acid.

10 Claims, 1 Drawing Figure

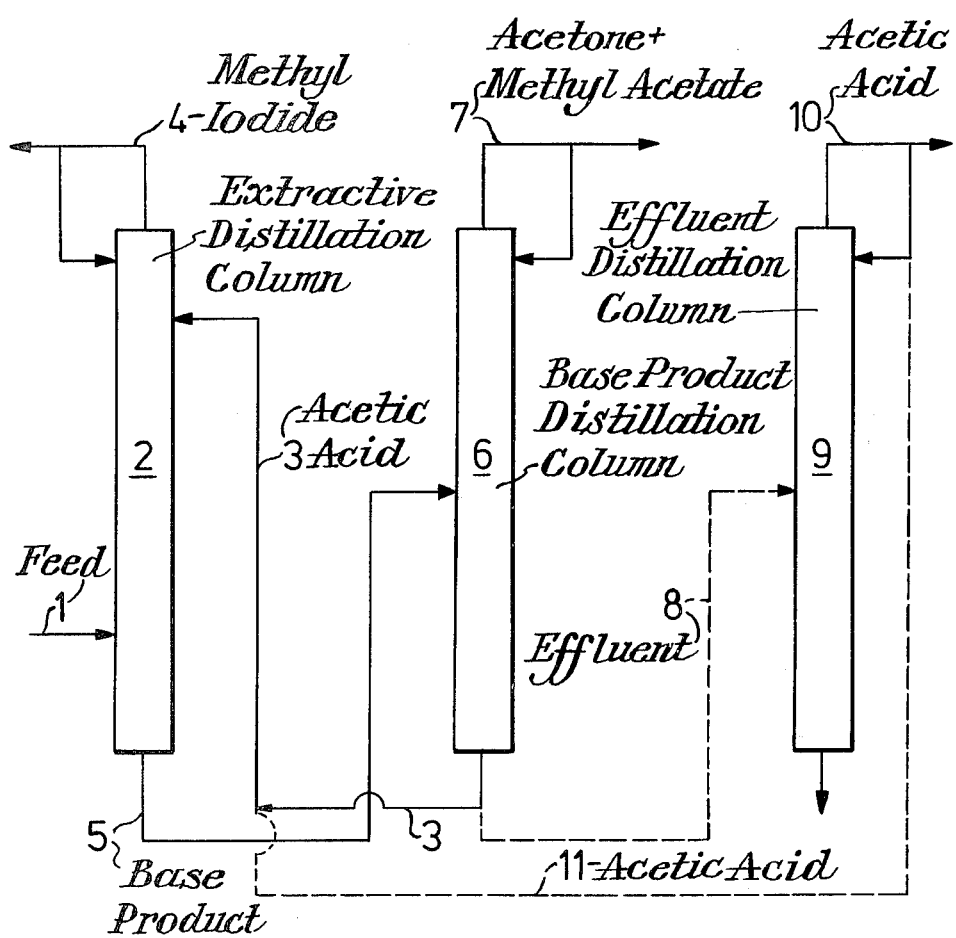

PROCESS FOR SEPARATING ACETONE FROM CARBONYLATION MIXTURES

The present invention relates to a process for separating acetone from reaction mixtures originating from the reaction of methyl acetate and/or dimethylether with carbon monoxide and optionally hydrogen in the presence of a catalyst system consisting of carbonyl complexes of noble metals of group VIII of the Periodic System of the elements, acetic acid, an organo-phosphorus or organonitrogen compound, methyl iodide and optionally compounds of carbonyl-yielding common metals (cf. e.g. DE-OS Nos. 24 50 965; 28 36 084; 29 39 839 and 29 41 232).

DE-OS No. 29 52 516 (=U.S. Pat. No. 4,252,748) describes a process for recovering acetone from the volatile constituents of a reaction mixture which is obtained by reaction of methyl acetate with carbon monoxide and hydrogen in the presence of a noble metal belonging to group VIII of the Periodic System of the elements and methyl iodide, the process comprising: establishing an at least 1:10 molar ratio of acetone to methyl iodide in the mixture of volatile constituents by introducing acetone into the carbonylation reaction; subjecting this mixture of volatile constituents to fractional distillation so as to separate practically all of the methyl iodide and a portion of the acetone and methyl acetate as distillate, the quantity of acetone separated corresponding practically to the quantity used in the reaction; distilling off remaining acetone and methyl acetate from the residue formed during distillation and recovering the acetone from the methyl acetate/acetone-mixture.

The acetone formed during the reaction is separated from the acetone/methyl acetate-mixture by azeotropic distillation with $C_5$-hydrocarbons (cf. U.S. Pat. No. 2,704,271) and extraction of the acetone/$C_5$-hydrocarbon-mixture with water, and fractionation of the acetone from the water phase. In this process, it is necessary for the quantity of acetone which has to be introduced into the carbonylation reaction together with cycled methyl iodide to correspond to the azeotropic composition of the methyl iodide/acetone-mixture.

The present invention compares favorably with these prior art methods in that the methyl iodide which is preferably recycled into the carbonylation reactor contains just very minor proportions of acetone, which adversely affects the activity of the catalyst and also effects undesirable formation of organic by-products.

The acetone is not easy to separate from the reaction mixture obtained after catalyst removal, or from a low boiler fraction thereof. The low boiler components comprised of methyl iodide, acetone and methyl acetate form azeotropic mixtures from which the individual pure components cannot be separated by fractional distillation. In addition to this, the pure components cannot be separated distillatively, or with extreme expense only, from the respective azeotropic mixture because of their very slightly different boiling points. Practically no difference exists, for example, between the 42.4° C. boiling point of the methyl iodide/acetone-azeotrope and the 42.5° C. boiling point of methyl iodide. Practically the same is true concerning the difference in the boiling points of the acetone/methyl acetate azeotrope (55° C.) and acetone (56.2° C.) or methyl acetate (57.2° C.).

The process of this invention comprises more especially: subjecting the reaction mixture containing acetic anhydride, acetic acid, ethylidene diacetate, methyl iodide, acetone and methyl acetate which is distilled off from the catalyst solution, or just its low boiler fraction consisting of methyl acetate, methyl iodide and acetone, wholly or partially to an extractive distillation with acetic acid and thereby distilling off pure methyl iodide and distilling off an acetone/methyl acetate mixture from the acetic acid extract; separating this mixture in known fashion and recycling the acetic acid extractant into the extraction stage, if desired after separation of the final reaction products comprised of acetic anhydride, ethylidene diacetate and acetic acid.

Further preferred features of the invention provide:
(a) for the reaction mixture distilled off from the catalyst solution to be extractively distilled with acetic acid in a ratio by weight of (0.75–7.5):1;
(b) for the low boilers comprised of methyl acetate, methyl iodide and acetone to be distilled off jointly from the reaction mixture distilled off from the catalyst solution, the low boilers being successively subjected to extractive distillation in a ratio by weight of low boilers to acetic acid of (0.5–5):1,
(c) for pure methyl iodide which is distilled off during the extractive distillation to be recycled to the carbonylation reaction;
(d) for the acetone/methyl acetate mixture to be admixed with $C_5$-hydrocarbons and for an acetone/$C_5$-hydrocarbon azeotrope to be distilled off;
(e) for the acetone/$C_5$-hydrocarbon azeotrope to be separated into its components by subjecting it to countercurrent extraction with water, the acetone being removed from the water by stripping, if desired;
(f) for the acetone/$C_5$-hydrocarbon azeotrope to be separated by extractive distillation with acetic acid into the $C_5$-hydrocarbon and an acetone/acetic acid mixture, the latter being separated into its components by fractional distillation;
(g) for pure methyl acetate which is retained during the distillation of the acetone/$C_5$-hydrocarbon azeotrope to be recycled to the carbonylation reaction.

Reaction mixture effluent from the carbonylation reactor is freed from gaseous products, such as unreacted carbon monoxide and, optionally, hydrogen as well as methane and carbon dioxide. Next, the catalyst system is distilled off inside an evaporator. The distillate is directly introduced in gaseous or preferably liquefied form into the extractive distilling column, if desired after prior separation into the low boilers comprised of methyl acetate, methyl iodide and acetone (as distillate) and into acetic acid, acetic anhydride and ethylidene diacetate as base products. In this latter case, the low boilers are introduced into the extractive distilling column. This is the point where the present invention sets out, which will now be described with reference to the accompanying flow scheme.

Catalyst-free reaction mixture or, if desired, its low boiler fraction is introduced through line 1 into the lower portion of extractive distilling column 2 comprising altogether 30 trays. The quantity of acetic acid necessary for effecting the extraction is introduced through line 3 at a level a few trays below the head of the column. Feed material and acetic acid are used in a ratio by weight of (0.5–7.5):1, based on the weight of reaction mixture or low boiler fraction used. Acetone-free methyl iodide is removed near the head of distilling column 2 through line 4 at 42°–43° C. at a reflux of 1–10, and introduced into the carbonylation reactor. The base product obtained in the extractive distilling column 2 is delivered through line 5 to column 6 comprising 15 trays, in which the acetone/methyl acetate-mixture is obtained as distillate through line 7 at a column head temperature of 56°–57° C. and at a reflux of 0.5–5. Upon the use of the above low boiler fraction, the effluent coming from the base portion of column 6 exclusively contains acetic acid which is recycled to column 2 through line 3. Upon the use of catalyst-free reaction mixture in extractive distilling column 2, the effluent coming from the base portion of column 6 contains acetic acid together with acetic anhydride and ethylidene diacetate, and it is introduced through line 8 into distilling column 9 comprising 40 trays, in which acetic acid is obtained as distillate through line 10 under a pressure of 150 millibars, at a column head temperature of 69°–70° C. and at a reflux of 0.1–5. After removal of produced acetic acid, it is recycled into extractive distilling column 2, through lines 11 and 3.

The acetone/methyl acetate-mixture is separated into its components in art-recognized fashion (not shown in the drawing) in a further column with the aid of a C$_5$-hydrocarbon mixture by azeotropic distillation. Acetone and C$_5$-hydrocarbon are used in a ratio by weight of 1:(5–8). The distillate is the acetone/C$_5$-hydrocarbon azeotrope and the base product is methyl acetate free from hydrocarbons, which is recycled to the carbonylation reactor. The acetone/C$_5$-hydrocarbon mixture is separated into its components in known fashion by subjecting it to countercurrent extraction with water, the acetone being removed from the water by stripping. As a novel alternative, the invention provides for the material to be subjected to further extractive distillation so as to obtain the C$_5$-hydrocarbon as distillate and an acetone/acetic acid-mixture as the base product, which can be separated into its components by fractional distillation.

EXAMPLE 1

9360 g reaction product was taken per hour from the carbonylation reactor. After separation of gaseous constituents and catalyst solution, 6170 g product containing about 0.3 wgt % acetone, 16.8 wgt % methyl iodide, 31.2 wgt % methyl acetate, 15.3 wgt % acetic acid, 36.2 wgt % acetic anhydride and 0.2 wgt % ethylidene diacetate was obtained. In order to be separated from the acetone, the product was metered on to the 10th tray of column 2 comprising altogether 30 trays, the column being operated at a base temperature of about 95° C., under a pressure of about 1 bar and at a reflux of 10. 2000 g/h acetic acid was given on to the 25th tray for acetone extraction. A temperature of 42° C. was found to establish at the column head. 1040 g/h distillate containing 99.8 wgt % methyl iodide and 0.2 wgt % methyl acetate as well as 7130 g base product containing about 0.27 wgt % acetone, 27 wgt % acetate, 41.3 wgt % acetic acid, 31.3 wgt % acetic anhydride and 0.15 wgt % ethylidene diacetate were obtained. The distillate was delivered to the carbonylation reactor. The base product coming from column 2 was decomposed in column 6 comprising 15 trays at a base temperature of 130°–135° C. and a head temperature of 57° C. and at a reflux of 3. 1950 g/h distillate containing about 1 wgt % acetone and 99 wgt % methyl acetate and 5180 g/h base effluent containing about 56.7 wgt % acetic acid, 43.1 wgt % acetic anhydride and 0.2 wgt % ethylidene diacetate were obtained.

The distillate was subjected in a further column to customary azeotropic distillation with n-pentane to remove the acetone. 170 g/h acetone/n-pentane-mixture which contained about 11.5 weight % acetone, i.e. the entire quantity of acetone, was obtained as the distillate at a column base temperature of 58° C. and head temperature of 34° C. and at a reflux of 20. 1930 g/h methyl acetate was obtained as the base product which was introduced into the carbonylation reactor. The acetone/n-pentane-mixture was introduced into an extraction column and extracted therein with the use of 350 g/h water. n-pentane obtained overhead was recycled to the azeotropic distilling column. 18 g/h acetone (as distillate) was separated from the acetone-containing effluent matter in a last column which was operated at atmospheric pressure, at a base temperature of 100° C. and head temperature of 56° C. at a reflux of 5. Water was the base product which was recycled to the extraction column.

In order to be freed from acetic acid, the base product coming from the acetone/methyl acetate-separating column 6 was introduced into fractionating column 9 operated under a pressure of 150 millibars. All the acetic acid used for the extraction and that formed during the reaction, altogether about 2940 g, were obtained at the head of column 9 at a column base temperature of 97° C. and head temperature of 69° C. at a reflux of 2 therein.

EXAMPLE 2

23 450 g/h reaction product was taken from the carbonylation reactor. Gaseous constituents, catalyst solution, acetic acid, acetic anhydride and ethylidene diacetate were separated, and 10 245 g/h low boiler mixture of 34.4 wgt % methyl iodide, 64.8 wgt % methyl acetate and 0.8 wgt % acetone was obtained which was recycled to the carbonylation stage except for a portion thereof. This portion of 1825 g/h was used for extracting acetone as described in Example 1. To this end, it was introduced into the base portion of column 2 which was fed overhead with 1000 g/h acetic acid. 629 g/h distillate containing 99.8 wgt % methyl iodide and 0.2 wgt % methyl acetate, and 2196 g/h base product containing about 0.7 wgt % acetone, 53.8 wgt % methyl acetate and 45.5 wgt % acetic acid were obtained at a base temperature of 74° C. and head temperature of 42° C., under a pressure of 1 bar and at a reflux of 10. The distillate was recycled to the carbonylation reactor. The base product effluent from column 2 was treated in column 6 at atmospheric pressure at a base temperature of 120° C. and head temperature of 57° C. at a reflux of 3, and 1196 g/h distillate containing about 1.25 wgt % acetone and 98.75 wgt % methyl acetate as well as 1000 g/h acetic acid (base product) were obtained, the acetic acid being recycled into column 2.

The acetone/methyl acetate mixture was introduced into the azeotropic distilling column for azeotropic removal of the acetone by means of pentane mixtures. 115 g/h distillate containing 13 wgt % acetone and 87 wgt % pentane was removed overhead at a column base temperature of 58° C. and head temperature of 34° C. at a reflux of 20. 1181 g/h methyl acetate effluent from the evaporator was recycled to the carbonylation reactor. The azeotropic mixture was subjected to further extractive distillation so as to separate acetone and pentane therefrom. To this end, 400 g/h acetic acid was introduced directly below the head, and the 115 g/h acetone/pentane mixture was introduced into the lower portion, of the column. The pentane mixture was obtained as the distillate and 415 g/h material containing about 3.6 weight % acetone and 96.4 wgt % acetic acid was obtained as the base product at a base temperature of 118° C. and head temperature of 36° C. at a reflux of 8. The acetone/acetic acid-mixture was introduced into a fractionating column which was operated at a base temperature of 120° C. and head temperature of 56° C. at a reflux of 3, and 15 g/h acetone was obtained as the distillate. The acetic acid coming from the evaporator was used again for extraction of the acetone/pentane-mixture.

EXAMPLE 3

A portion of the low boiler mixture consisting of the carbonylation products of Example 2, namely 1151 g/h containing 2.1 wgt % acetone, 86.1 wgt % methyl iodide and 11.8 wgt % methyl acetate was introduced into the base portion of column 2. 1000 g/h acetic acid for acetone extraction was introduced immediately below the head of the column. 991 g/h methyl iodide was obtained at a base temperature of 73° C. and head temperature of 43° C. at a reflux of 8. It was recycled to the carbonylation reactor. The base product was comprised of 1160 g/h mixture with about 2.1 wgt % acetone, 11.7 wgt % methyl acetate and 86.2 wgt % acetic acid, and was introduced into column 6, in which 160 g/h distillate containing about 15 wgt % acetone and 85 wgt % methyl acetate and 1000 g/h acetic acid (base product) were obtained at a column base temperature of 120° C. and head temperature of 57° C. at a reflux of 3.

The acetic acid was recycled into column 2 whilst the distillate was separated into its components in the azeotropic distilling column with addition of pentane. 174 g/h distillate containing 13.8 wgt % acetone and 86.2 wgt % pentane as well as 136 g/h methyl acetate (base product) were obtained at a column base temperature of 58° C. and head temperature of 34° C. at a reflux of 20. The acetone/pentane-mixture was separated into its components in an extraction column, in which the mixture was treated with 140 g/h water. The pentane issuing at the head was recycled to the azeotropic distilling column, the base product effluent being introduced into a further fractionating column, in which 24 g/h acetone was separated at a column base temperature of 100° C. and head temperature of 56° C. at a reflux of 3. The water was recycled to the extraction stage.

We claim:

1. A process for separating acetone from a reaction mixture originating from the carbonylation reaction of at least one substance selected from the group consisting of methyl acetate and dimethylether with a coreactant comprising carbon monoxide in the presence of a catalyst solution containing carbonyl complexes of noble metals belonging to Group VIII of the Periodic System of the elements, acetic acid, an organophosphorus or organonitrogen compound and methyl iodide, which comprises: subjecting a said reaction mixture containing acetic anhydride, acetic acid, ethylidene diacetate, methyl iodide, acetone and methyl acetate, which has been distilled off from the catalyst solution, to an extractive distillation step with acetic acid as extractant, thereby forming an acetic acid extract base product and distilling off essentially pure methyl iodide; distilling off an acetone/methyl acetate-mixture from the acetic acid extract base product and separating said mixture and recycling the acetic acid extractant remaining in the base product into said extractive distillation step after separation of the reaction products of the caronbylation reaction comprised of acetic anhydride, ethylidene diacetate and acetic acid.

2. A process for separating acetone from a reaction mixture originating from the carbonylation reaction of at least one substance selected from the group consisting of methyl acetate and dimethylether with a coreactant comprising carbon monoxide in the presence of a catalyst solution containting carbonyl complexes of noble metals belonging to group VIII of the Periodic System of the elements, acetic acid, an organophosphorus or organonitrogen compound and methyl iodide, which comprises: subjecting a low boiler fraction having been distilled off from the catalyst solution and a said reaction mixture and consisting essentially of methyl acetate, methyl iodide and acetone to an extractive distillation step with acetic acid as extractant, thereby forming an acetic acid extract base product and distilling off essentially pure methyl iodide; distilling off an acetone/methyl acetate-mixture from the acetic acid extract base/product and separating said mixture; and recycling the acetic acid extractant remaining in the base product into said extractive distillation step.

3. A process as claimed in claim 1, wherein said coreactant contains hydrogen.

4. A process as claimed in claim 1, wherein the catalyst solution additionally contains carbonyl-yielding compounds of common metals.

5. A process as claimed in claim 1, wherein the reaction mixture distilled off from the catalyst solution is extractively distilled with acetic acid in a ratio by weight of (0.75–7.5):1.

6. A process as claimed in claim 2, wherein the low boiler fraction is distilled off from the reaction mixture distilled off from the catalyst solution, the low boiler fraction being subsequently subjected to extractive distillation in a ratio by weight of low boiler fraction to acetic acid of (0.5–5):1.

7. A process as claimed in claim 1, wherein the essentially pure methyl iodide distilled off during said extractive distillation step is recycled into the catalyst solution.

8. A process as claimed in claim 2, wherein said coreactant contains hydrogen.

9. A process as claimed in claim 2, wherein the catalyst solution additionally contains carbonyl-yielding compounds of common metals.

10. A process as claimed in claim 2, wherein the essentially pure methyl iodide distilled off during the extractive distillation is recycled into the catalyst solution.

* * * * *